US00PP22088P2

(12) United States Plant Patent
Dickerson

(10) Patent No.: US PP22,088 P2
(45) Date of Patent: Aug. 23, 2011

(54) ***JUNIPERUS* PLANT NAMED 'NEWBOLD'**

(50) Latin Name: *Juniperus chinensis×virginiana*
Varietal Denomination: Newbold

(76) Inventor: David Dickerson, Hawthorne, FL (US)

( * ) Notice: Subject to any disclaimer, the term of this patent is extended or adjusted under 35 U.S.C. 154(b) by 0 days.

(21) Appl. No.: 12/592,570

(22) Filed: Nov. 27, 2009

(51) Int. Cl.
*A01H 7/00* (2006.01)

(52) U.S. Cl. ..... Plt./214

(58) Field of Classification Search ..... Plt./214
See application file for complete search history.

(56) References Cited

OTHER PUBLICATIONS

Oregon State University, Dept. of Horticulture; Landscape Plants—Images, Identification and Information; vol. 2, 1999-2010, pp. 1-33.*

* cited by examiner

*Primary Examiner* — Susan McCormick Ewoldt

(57) ABSTRACT

A new and distinct *Juniperus chinensis×virginiana* cultivar named 'NEWBOLD' is disclosed, characterized by a distinctive blue cast to the foliage, unique spatial spread of the foliage, and a broad spreading habit of the plant canopy. The new variety shows resistance to foliar diseases typical of *Juniperus* species in a Northern Florida climate. The new variety also shows resistance to foliar damage caused by mites. The new variety is a *Juniperus*, and is normally used as a garden or landscape plant.

2 Drawing Sheets

Figure 1:
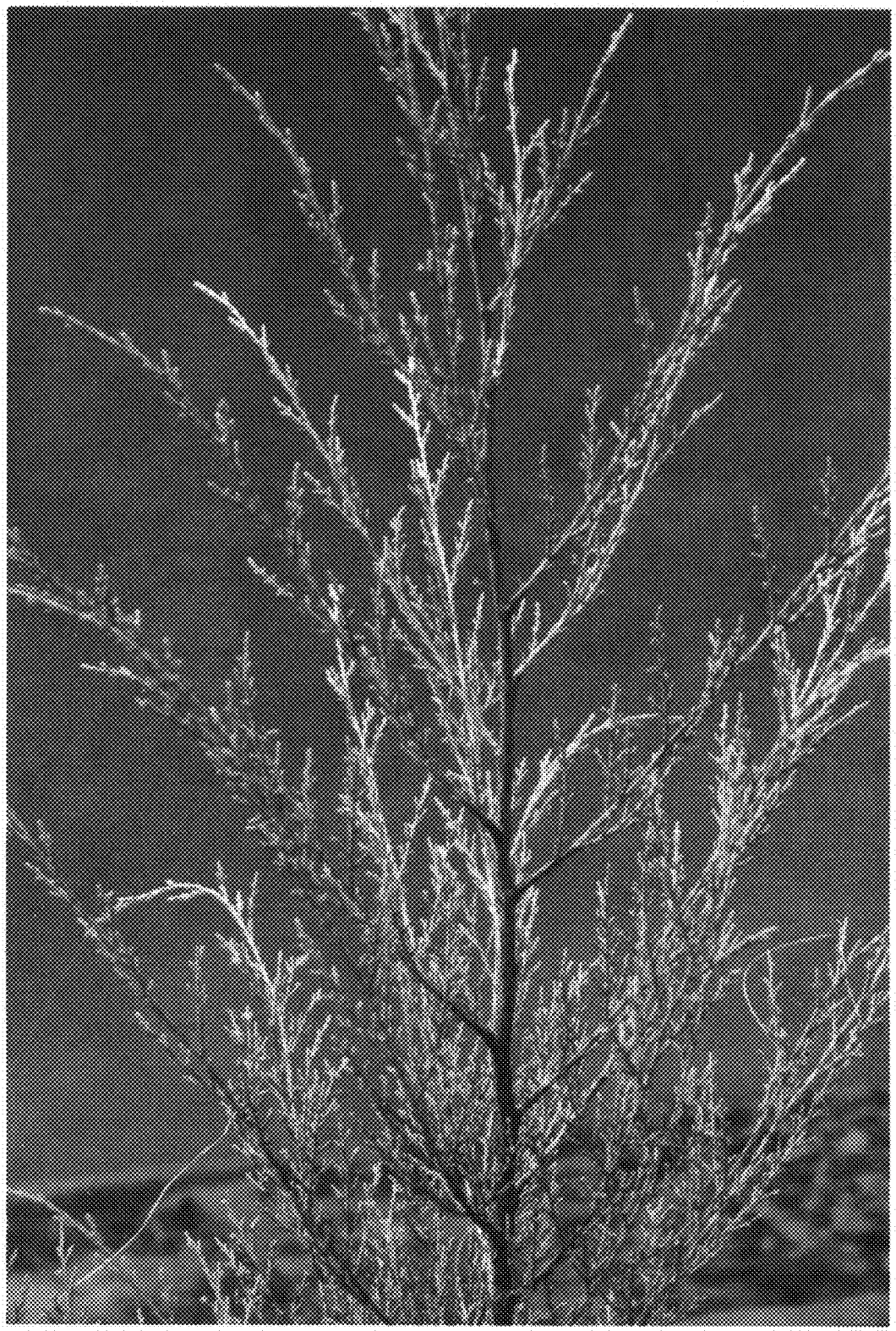

Latin name of the genus and species: *Juniperus chinensis× virginiana.*

Variety denomination: 'NEWBOLD'.

BACKGROUND OF THE INVENTION

The new cultivar was discovered as a chance seedling, in a commercial nursery in Hawthorne, Fla. The inventor, David Dickerson, a citizen the United States, discovered the new variety as a seedling among several plants of the unpatented varieties, *Juniperus virginiana* and *Juniperus chinensis*. The new variety was discovered in April of 2005 by the inventor. After discovery the inventor observed and propagated the variety in the controlled environment of his nursery in Hawthorne, Fla. After approximately 5 years of observation, the inventor noted characteristics of both *Juniperus virginiana* and *Juniperus chinensis* in the new variety. For this reason, the inventor believes, to the best of his knowledge, the new variety to be an inter-specific cross between *Juniperus virginiana* and *Juniperus chinensis*. This is not a known fact as the new variety is the result of a chance crossing rather than a controlled crossing.

Asexual reproduction of the new cultivar 'NEWBOLD' by vegetative cuttings was performed at the nursery in Hawthorne, Fla. in October of 2005. Vegetative reproduction by cuttings has produced multiple generations, and has shown that the unique features of this cultivar are stable and reproduced true to type through successive generations.

SUMMARY OF THE INVENTION

The cultivar 'NEWBOLD' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NEWBOLD.'

These characteristics in combination distinguish 'NEWBOLD' as a new and distinct *Juniperus* hybrid cultivar:

1. Distinctive blue color cast to the foliage.
2. Unique spatial spread of the foliage.
3. Broad spreading habit of the plant canopy.
4. Resistance to disease typical of *Juniperus* species in the Northern Florida climate.
5. Resistance to foliar damage caused by mites.

PARENT COMPARISON

Plants of the new cultivar 'Newbold' are similar to plants of the parent variety *Juniperus chinensis* in most horticultural characteristics. However, the new cultivar 'NEWBOLD' forms more overall symmetrical, regularly shaped plants, whereas *Juniperus chinensis* is characteristically forming irregular overall plant shapes. Additionally, the new variety has a greater spacing in the foliage; individual branches and scales are less tightly held. This unique spatial spread of the foliage, to the best of the inventor's knowledge, gives the new variety better resistance to disease.

Plants of the new cultivar 'Newbold' are similar to plants of the parent variety *Juniperus virginiana* in most horticultural characteristics. However, plants of the new cultivar 'NEWBOLD' have foliage with a significantly more blue coloration. Additionally, the new variety has a better overall plant vigor than *Juniperus virginiana* and forms a more open branch canopy.

COMMERCIAL COMPARISON

'NEWBOLD' is best compared to the parent varieties.

BRIEF DESCRIPTION OF THE PHOTOGRAPH

The accompanying photograph in FIG. 1 illustrates in full color a typical foliage branch of 'NEWBOLD' grown outdoors in Hawthorne, Fla.

Figure 2:
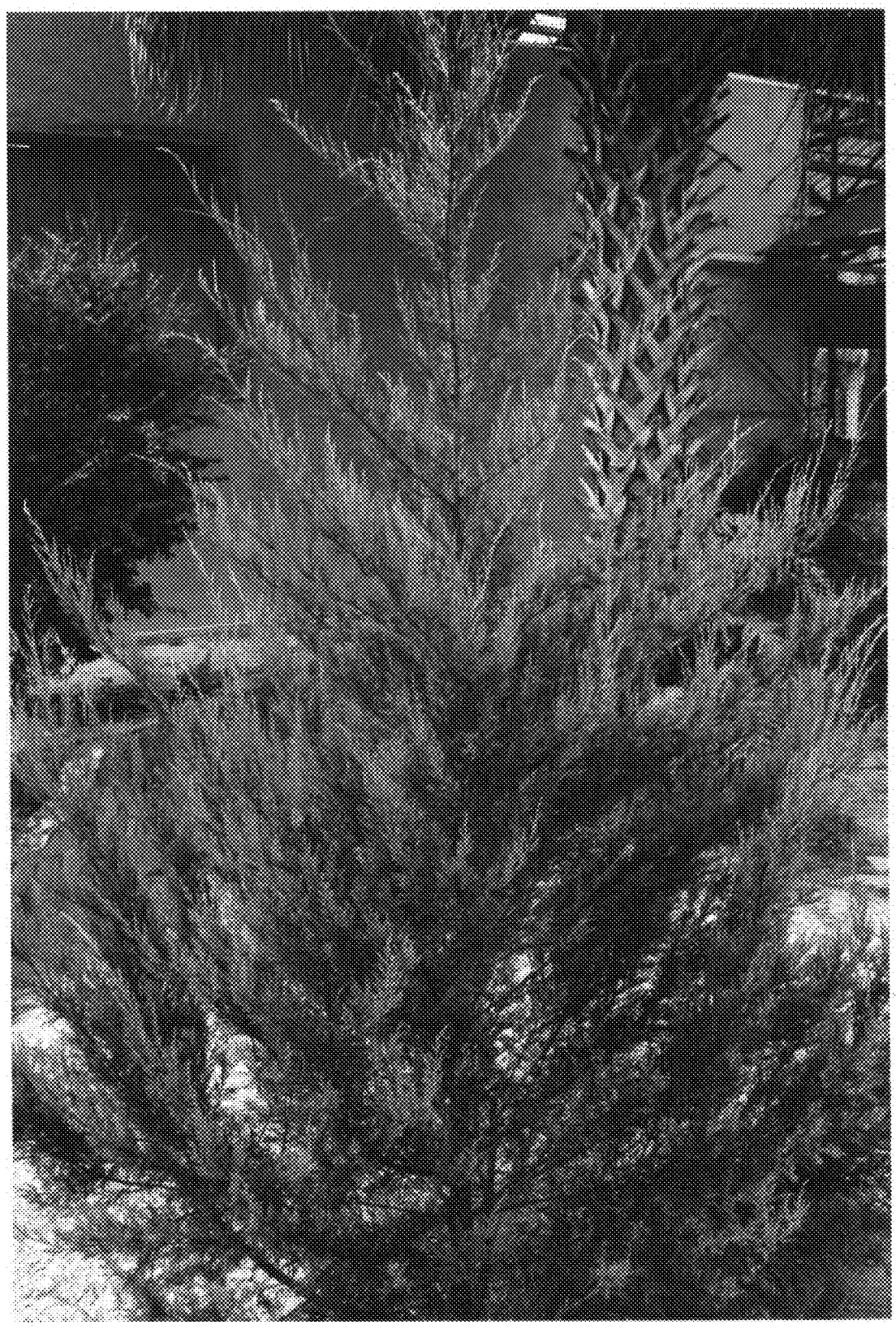

FIG. 2 illustrates in full color a typical plant of 'NEWBOLD.' The plant is growing in the ground and approximately 3 years old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'NEWBOLD' plants grown outdoors in Hawthorne, Fla. Year round temperature ranged from approximately 16 to 100° F., with naturally high light conditions. Measurements and numerical values represent averages of typical flowering types. No chemical or photoperiodic treatments were given.

Botanical classification: *Juniperus chinensis×virginiana* 'NEWBOLD.'

Age of plant described: Approximately 10 months old, planted in a 1 gallon pot.

PROPAGATION

Root description: Fine, well-branched, fibrous, becoming slightly woody with age.

PLANT

Growth habit: Upright, woody evergreen.

Height: Approximately 75 cm, from soil line.

Plant spread: Approximately 21 cm.

Growth rate: Rapid, approximately 2 to 3 feet in one year under optimum conditions.

Branching characteristics: Free branching.

Length of lateral branches: Lower lateral branches average 35 cm, upper lateral branches average 15 cm.

Diameter of lateral branches: Approximately 0.4 cm.

Quantity of lateral branches: Approximately 25 to 30.

Texture of lateral branches: Woody, scaly.

Color of lateral branches: Near RHS Grey-Brown N199B

Aspect: Straight, occurring at approximately 15° angle, from stem, angle increases significantly with age.

Strength of lateral branches: Very strong.

Internode length: Approximately 2.8 cm.

FOLIAGE

Leaf:

*Arrangement.*—Decussate. Immature foliage tightly pressed. Mature foliage individual needles.

Individual needles:

*Average length.*—Approximately 0.5 cm.

*Average width.*—Approximately 0.1 cm.

*Shape of blade.*—Awl-like.

*Apex.*—Acute, sharp to the touch.

*Base.*—Truncate.

*Attachment.*—Sessile.

*Margin.*—Entire.

*Texture of top surface.*—Smooth, matte.

*Texture of bottom surface.*—Smooth, matte.

*Leaf internode length.*—Approximately 0.15 cm.

*Color.*—Young foliage upper side: Near RHS Green 139B. Young foliage under side: Near RHS Green 139B. Mature foliage upper side: Near RHS Green 133B. Mature foliage under side: Near RHS Green 133B.

*Venation.*—Type: Linear. Venation color: Indistinguishable from foliage color.

Cone description: Cone Production not observed.

OTHER CHARACTERISTICS

Disease resistance: Resistance to normal foliar diseases normal to *Juniperus*, have been observed in this variety.

Drought tolerance and temperature tolerance: Low temperature tolerance to approximately USDA Zone 4. Tolerates high temperature extremely well, to at least 40° C. Some drought tolerance. Plants can be allowed in dry soil for several days without damage.

Fruit/seed production: Fruits and seeds have not been observed.

What is claimed is:

1. A new and distinct cultivar of *Juniperus* plant named 'NEWBOLD' as herein illustrated and described.

* * * * *